United States Patent [19]

Wilk

[11] Patent Number: 5,258,008
[45] Date of Patent: Nov. 2, 1993

[54] SURGICAL STAPLING DEVICE AND ASSOCIATED METHOD

[76] Inventor: Peter J. Wilk, 185 West End Ave., New York, N.Y. 10023

[21] Appl. No.: 921,510

[22] Filed: Jul. 29, 1992

[51] Int. Cl.⁵ .............................................. A61B 17/00
[52] U.S. Cl. .................................... 606/219; 227/175; 227/177; 227/179
[58] Field of Search .................. 606/142, 143, 219; 227/19, 175-179

[56] References Cited

U.S. PATENT DOCUMENTS

| | | | |
|---|---|---|---|
| 4,473,077 | 9/1984 | Noiles | 227/179 |
| 4,477,007 | 10/1084 | Foslien | 227/19 |
| 4,485,817 | 12/1984 | Swiggett | 227/179 |
| 4,488,523 | 12/1984 | Shichman | 227/179 |
| 5,042,707 | 8/1991 | Taheri | 227/179 |

Primary Examiner—Stephen C. Pellegrino
Assistant Examiner—Gary Jackson
Attorney, Agent, or Firm—R. Neil Sudol; Henry D. Coleman

[57] ABSTRACT

A multiple fire surgical stapler comprises an elongate frame and a pair of jaws movably secured to one another at a proximal end and to the frame at a distal end thereof. Each of the jaws includes a plurality of segments movably secured to one another, whereby the jaws can alternately assume different configurations. A plurality of staples is mounted to one of the jaws, while a firing mechanism is operatively connected to the frame for firing the staples to close the staples.

20 Claims, 1 Drawing Sheet

SURGICAL STAPLING DEVICE AND ASSOCIATED METHOD

BACKGROUND OF THE INVENTION

This invention relates to a surgical stapling device and an associated method. This invention also relates to an endoscopic stapling device and an associated method. More specifically, this invention relates to a multiple fire stapling device, which may be configured for use with endoscopes.

U.S. Pat. No. 5,015,249 to Nakao et al. discloses an endoscopic stapling device which enables a staple to be applied to internal body tissues at a distal end of an endoscope insertion member which has been inserted into a patient. This stapler, however, allows only one staple to be fired at a time.

Surgical staplers for anastomoses exist wherein multiple staples in linear arrays are fired between jaws which are maintained in a closed configuration during the firing of the staples. The staples are fired sequentially by an ejector rod with a camming surface at a distal end. As the rod is pushed in the distal direction, the staples are pushed in sequence from one jaw against the other jaw, which serves to close the staples in a conventional process.

Anastomoses staplers include multiple rows of staples, with a cutting blade disposed between adjacent rows. The blade is actuated subsequently to the firing of the staples and prior to the removal of the stapled organic tissues from between the stapler jaws.

OBJECTS OF THE INVENTION

An object of the present invention is to provide an endoscopic stapler which is capable of firing multiple staples in a predetermined pattern.

Another object of the present invention is to provide an associated endoscopic stapling method.

Another, more particular, object of the present invention is to provide a multiple fire surgical stapler with means for varying the configuration of staples.

These and other objects of the present invention will be apparent from the drawings and detailed descriptions herein.

SUMMARY OF THE INVENTION

A multiple fire surgical stapler comprises, in accordance with the present invention, an elongate frame and a pair of jaws movably secured to one another at a proximal end and to the frame at a distal end thereof. Each of the jaws includes a plurality of segments movably secured to one another, whereby the jaws can alternately assume different configurations. The stapler further comprises a plurality of staples mounted to one of the jaws and a firing mechanism operatively connected to the frame for firing the staples to close the staples.

Pursuant to another feature of the present invention, the surgical stapler includes a mechanism for stiffening or rigidifying the jaws prior to an actuation of the firing mechanism. The stiffening or rigidifying mechanism serves to rigidify the jaws in a predetermined configuration, for example, a linear configuration.

Where the stapler is to be used in endoscopic surgical procedure, the frame is flexible and has a diameter smaller than a biopsy channel of an endoscope. The structuring of the jaws as a series of segments movably connected to each other enables insertion of the stapling device into a patient while the stapling device is disposed in the biopsy channel an endoscope. The stiffening mechanism enables the jaws to assume a predetermined configuration upon ejection of the jaws from the distal end of the endoscope and prior to firing of the staples about internal body tissues.

Pursuant to another feature of the present invention, the jaw segments are provided with mating projections and recesses, the projections being slidably inserted into corresponding recesses.

Where the staples are arrayed in a plurality of parallel rows, a severing device such as a flexible blade is disposed in part between a pair of the rows for severing tissues stapled between the rows of the pair upon actuation of the firing mechanism.

A multiple fire surgical stapler comprises, in accordance with another conceptualization of the present invention, an elongate frame, a pair of jaws movably secured to one another at a proximal end and to the frame at a distal end thereof, and a plurality of staples mounted to one of the jaws. Elements are provided on the jaws for enabling a bending of the jaws during an endoscopic insertion procedure, while a firing mechanism is operatively connected to the frame for firing the staples to close the staples. In addition, a rigidifying mechanism is operatively connected to the frame and the jaws for stiffening the jaws prior to an actuation of the firing mechanism.

A method for use in a surgical procedure comprises, in accordance with the present invention, the steps of (a) providing a pair of jaws movably secured to one another at a proximal end, (b) bending the jaws along their respective lengths, (c) rigidifying the jaws so that each assumes a predetermined configuration, (d) disposing the jaws about internal body tissues of a patient, (e) firing a plurality of staples from one of the jaws through the surrounded internal body tissues and against the other of the jaws, and (f) closing the staples so that the staples are arrayed in the internal body tissues in the predetermined configuration assumed by the jaws during the step of rigidifying.

Where each of the jaws includes a plurality of segments movably secured to one another, the step of bending the jaws includes the step of pivoting the segments relative to each other, whereby each of the jaws assumes different configurations at successive times.

Pursuant to another feature of the present invention, the method further comprises the step of inserting the jaws through the biopsy channel of an endoscope, the step of bending occurring at least in part during insertion of the jaws through a tubular internal organ of the patient.

The present invention provides an endoscopic stapler which is capable of firing multiple staples in a predetermined pattern. The jaws are bendable to an extent which enables insertion of the stapler with an endoscope into a patient's colon, for example.

DETAILED DESCRIPTION

Figure 1:
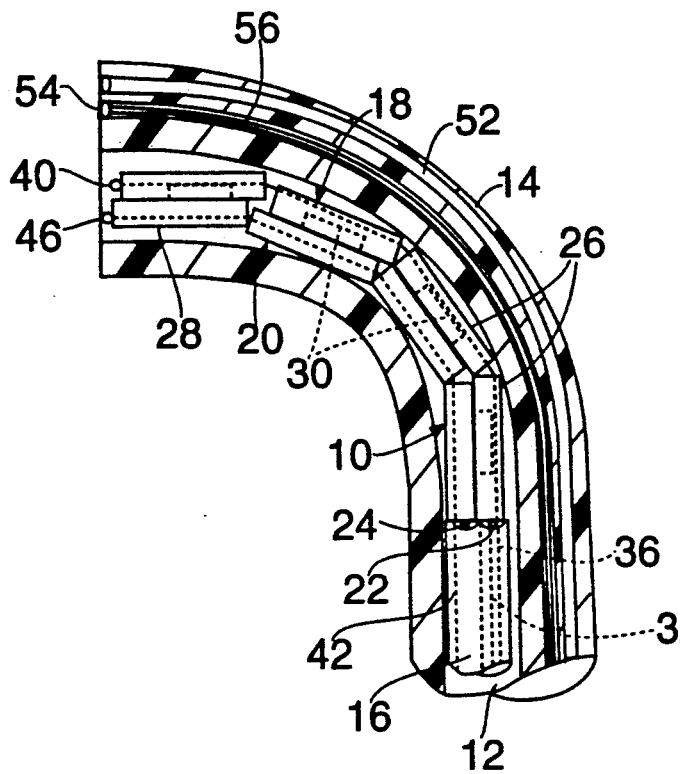
FIG. 1 is a partial schematic longitudinal cross-sectional view, on an enlarged scale, through a distal end of an endoscope insertion member, showing an endoscopic multiple fire stapling device in accordance with the present invention.

FIG. 1 illustrates a multiple fire surgical stapler 10 inserted in a biopsy channel 12 of a flexible endoscope insertion member 14. Stapler 10 comprises an elongate flexible frame or shaft 16 and a pair of jaws 18 and 20 movably secured to one another and to shaft 16 at one or more pivot pins 22 and 24. Each jaw 18 and 20 includes a plurality of segments 26 and 28 movably secured to one another, whereby jaws 18 and 20 can alternately assume different configurations such as an arcuate configuration shown in FIG. 1.

Stapler 10 further comprises a plurality of staples 30 mounted to jaw 18 for ejection towards jaw 20 under the action of a firing mechanism including a flexible rod 32 operatively connected to and longitudinally traversing shaft 16. A distal end of rod 32 is provided with a camming surface 34 (FIG. 2) for engaging and ejecting staples 30 in a transverse direction upon a longitudinal motion of rod 32.

Surgical stapler 10 additionally includes a mechanically acting tensioning device or wire 36 extending through channels 38 in segments 26 and fastened at a distal end 40. Wire 36 serves to stiffen or rigidify jaw 18 in a linear configuration prior to an actuation of firing rod 32. Similarly, another tensioning device or wire 42 extending through channels (not illustrated) in segments 28 and fastened at a distal end 46 serves to rigidify jaw 20 in a linear configuration prior to a multiple fire stapling operation.

Figure 2:
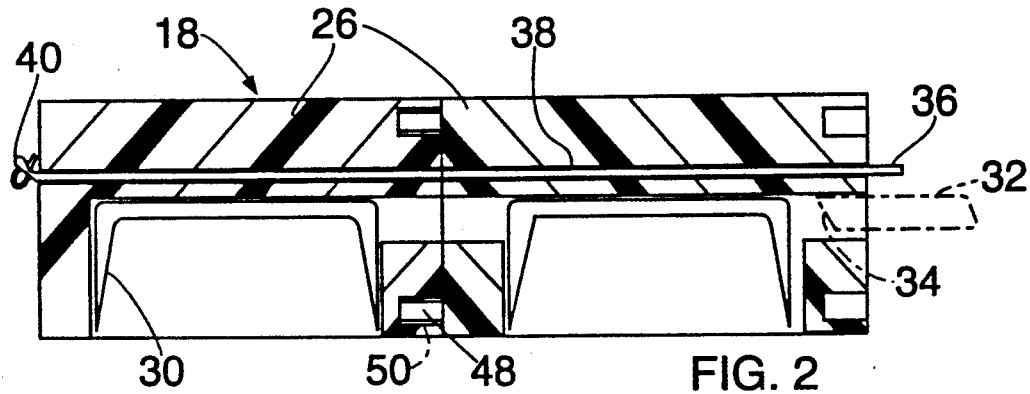
FIG. 2 is a partial schematic longitudinal cross-sectional view, on a larger scale, of a distal end portion of the endoscopic multiple fire stapling device of FIG. 1.

As illustrated in FIG. 2, jaw segments 26 are provided with mating projections 48 and recesses 50, projections 48 being slidably inserted into corresponding recesses 50.

Shaft 16 is flexible and has a diameter smaller than biopsy channel 12. Upon an insertion of endoscope insertion member 14 with stapler 10 into a patient's colon, for example, illuminating radiation is conducted into the patient via an illumination light guide 52. Light reflected from internal organic structures of the patient is then focused by a lens 54 onto a distal end of a fiber optic image guide 56. In response to images transmitted to an eyepiece (not shown) or monitor (not shown) via image guide 56, a surgeon or endoscopist pushes tubular shaft 16 to eject jaws 18 and 20 from the distal end of insertion member 14. Either prior to or after the ejection, wires 36 and 42 are pulled in the proximal direction to straighten and rigidify jaws 18 and 20.

Upon ejection of jaws 18 and 20 and the stiffening thereof via wires 36 and 42, the jaws are opened, for example, by continued tension on wires 36 and 42. Alternatively, additional tension elements or biasing springs (not illustrated) may be provided for opening jaws 18 and 20. Jaws 18 and 20 are then disposed about tissues to be stapled. Closure may be effectuated by pushing an auxiliary tubular member (not shown) about the jaws. Alternatively, the jaws may be operated as conventional endoscopic forceps.

Upon the closure of jaws 18 and 20 about the target tissues, rod 32 is shifted in the distal direction through to eject staples 30 from jaw 18. Staples 30 are closed by being forced against camming anvils (not illustrated) in jaw 20. Such camming anvils take a well known conventional form.

It is to be noted that the segments 26 (28) of jaw 18 (20) are articulated to one another. Accordingly, jaws 18 and 20 are bent during insertion into a patient by pivoting segments 26 and 28 relative to each other, whereby each of the jaws assumes different configurations at successive times.

Figure 3:
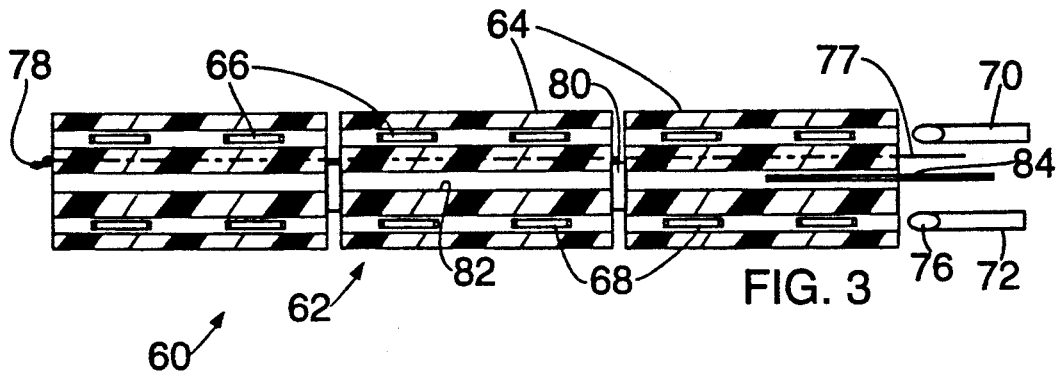
FIG. 3 is a partial schematic longitudinal cross-sectional view, on an enlarged scale, of a distal end portion of another multiple fire stapling device in accordance with the present invention.

As illustrated in FIG. 3, another multiple fire surgical stapler 60 comprises a jaw 62 including a plurality of articulated or pivoted segments 64 for enabling jaw 62 to alternately assume a straight and different arcuate configurations.

Stapler 60 further comprises a first plurality of staples 66 arranged in a first row and a second plurality of staples 68 disposed in a second row parallel to staples 66. Staples 66 and 68 are ejectable towards an anvil carrying jaw (not shown) under the action of a pair of firing rods 70 and 72 each including a camming surface 74 and 76 at a distal end. Rods 70 and 72 are operatively connected to and longitudinally traversing a shaft (not shown) to which jaw 62 is pivotably connected.

Surgical stapler 60 additionally includes a mechanically acting tensioning device or wire 77 extending through segments 64 and fastened at a distal end 78. Wire 76 serves to stiffen or rigidify jaw 62 in a linear configuration prior to an actuation of firing rods 70 and 72 in a multiple firing operation.

As illustrated in FIG. 3, jaw segments 64 are provided with projections 80 slidably extending into corresponding recesses (not shown). Segments 64 are provided with longitudinally extending and alignable slots 82 for receiving a cutting blade 84 upon a common ejection stroke of rods 70 and 72.

In the event that stapler 60 is an endoscopic device, blade 84 is sufficiently flexible to allow for bending during an endoscopic insertion procedure.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that although the stapler of the present invention has been developed primarily for endoscopic purposes, it may also find use in larger staplers with rigid shafts. In addition, it is possible to rigidify the stapler jaws in a desired arcuate configuration for stapling along an arc rather than a line. Accordingly, it is to be understood that the drawings and descriptions herein are profferred by way of example to facilitate comprehension of the invention and should not be construed to limit the scope thereof.

What is claimed is:

1. A multiple fire surgical stapler comprising:
   an elongate frame;
   a pair of jaws movably secured to one another at a proximal end and to said frame at a distal end thereof, each of said jaws including a plurality of segments movably secured to one another, whereby said jaws can alternately assume different configurations;
   a plurality of staples mounted to one of said jaws; and
   firing means operatively connected to said frame for firing said staples to close said staples.

2. The stapler defined in claim 1, further comprising means for stiffening said jaws prior to an actuation of said firing means.

3. The stapler defined in claim 2 wherein said means for stiffening serves to rigidify said jaws in a predetermined configuration.

4. The stapler defined in claim 3 wherein said predetermined configuration is linear.

5. The stapler defined in claim 1 wherein said segments are provided with mating projections and recesses, the projections being slidably inserted into corresponding recesses.

6. The stapler defined in claim 1 wherein said staples are arrayed in a plurality of parallel rows.

7. The stapler defined in claim 1, further comprising severing means disposed in part between a pair of said rows for severing tissues stapled between the rows of said pair upon actuation of said firing means.

8. The stapler defined in claim 1 wherein said frame is flexible and has a diameter smaller than a biopsy channel of an endoscope, whereby the stapler may be used in conjunction with the endoscope to perform an endoscopic surgical operation.

9. A multiple fire surgical stapler comprising:
an elongate frame;
a pair of jaws movably secured to one another at a proximal end and to said frame at a distal end thereof;
a plurality of staples mounted to one of said jaws;
means on said jaws for enabling a bending of said jaws during an endoscopic insertion procedure;
firing means operatively connected to said frame for firing said staples to close said staples; and
means operatively connected to said frame and to said jaws for stiffening said jaws prior to an actuation of said firing means.

10. The stapler defined in claim 9 wherein said means for stiffening serves to rigidify said jaws in a predetermined configuration.

11. The stapler defined in claim 10 wherein said predetermined configuration is linear.

12. The stapler defined in claim 9 wherein each of said jaws includes a plurality of segments movably secured to one another, said means for enabling including mating projections and recesses on said segments, the projections being slidably inserted into corresponding recesses.

13. The stapler defined in claim 9 wherein said staples are arrayed in a plurality of parallel rows.

14. The stapler defined in claim 9, further comprising severing means disposed in part between a pair of said rows for severing tissues stapled between the rows of said pair upon actuation of said firing means.

15. The stapler defined in claim 9 wherein said frame is flexible and has a diameter smaller than a biopsy channel of an endoscope, whereby the stapler may be used in conjunction with the endoscope to perform an endoscopic surgical operation.

16. A method for use in a surgical procedure, comprising the steps of:
providing a pair of jaws movably secured to one another at a proximal end;
bending said jaws along their respective lengths;
rigidifying said jaws so that each assumes a predetermined configuration;
disposing said jaws about internal body tissues of a patient;
firing a plurality of staples from one of said jaws through the surrounded internal body tissues and against the other of said jaws; and
closing said staples so that said staples are arrayed in said internal body tissues in the predetermined configuration assumed by said jaws during said step of rigidifying.

17. The method defined in claim 16 wherein said jaws each includes a plurality of segments movably secured to one another, said step of bending including the step of pivoting said segments relative to each other, whereby each of said jaws assumes different configurations at different times.

18. The stapler defined in claim 16 wherein said predetermined configuration is linear.

19. The stapler defined in claim 16 wherein said staples are arrayed in a plurality of parallel rows.

20. The method defined in claim 16, further comprising the step of inserting said jaws through the biopsy channel of an endoscope, said step of bending occurring at least in part during insertion of said jaws through a tubular internal organ of the patient.

* * * * *